United States Patent [19]

Bodor

[11] 3,998,815
[45] Dec. 21, 1976

[54] 1-HYDROCARBONOYLOXYMETHYL-3-CARBAMOYL OR 3-CARBOETHOXY-PYRIDINIUM SALTS

[75] Inventor: Nicolae S. Bodor, Lawrence, Kans.

[73] Assignee: Interx Research Corporation, Lawrence, Kans.

[22] Filed: June 24, 1974

[21] Appl. No.: 482,513

[52] U.S. Cl. .................. 260/240 K; 260/298 SA; 260/295.5 R; 260/309; 260/468 R; 260/477; 260/240 J; 260/490; 260/268 B; 424/266; 424/305
[51] Int. Cl.² .................................... C07D 213/20
[58] Field of Search ............. 260/295.5 A, 295.5 R, 260/240 K

[56] References Cited
OTHER PUBLICATIONS

Ulich et al., J.A.C.S. vol. 43, (1921), pp. 660–667.
Daehne et al., J. of Med. Chem., (1970), vol. 13, No. 4, pp. 607–612.
Etienne et al., Chem. Abst. vol. 77, (1972), 164403.

Primary Examiner—Natalie Trousof
Assistant Examiner—Bernard I. Dentz
Attorney, Agent, or Firm—Charles N. Blitzer

[57] ABSTRACT

Labile quaternary ammonium salts of the following formula (I) and (II) are provided:

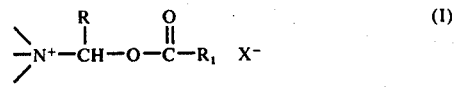

(I)

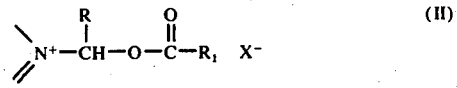

(II)

wherein $\equiv N$ represents a tertiary aliphatic amine;
wherein $\supset\!\!\!N$ represents an aromatic amine; wherein R represents a member selected from the group consisting of a hydrogen atom, a $C_1$-$C_8$ open chain or cyclo alkyl group, a $C_1$-$C_8$ alkoxyalkyl group, a $C_1$-$C_8$ acyloxyalkyl group, a $C_1$-$C_8$ haloalkyl group, a $C_1$-$C_8$ carboxyalkyl group, an aryl group, and a substituted aryl group, whose substituents are selected from the group consisting of a halogen atom, an O-lower alkyl ($C_1$-$C_4$) group, an O-acyl group, a nitro group, a carboxyl group, and a carboethoxy group; wherein $R_1$ which may be the same or different, represents any member defined by R above with the proviso that $R_1$ cannot be a hydrogen atom; and wherein $X^-$ represents a member selected from the group consisting of a halogen atom or any other equivalent anion;

with the further proviso that $\equiv N$ and $\supset\!\!\!N$, respectively cannot represent trimethylamine and pyridine or quinoline when R represents a hydrogen atom and $R_1$ represents a methyl group or a phenyl group.

The compounds described above are characterized by their extreme solubility and resistance to oxidation, dealkylation, and protonation prior to chemical and/or enzymatic hydrolysis. Upon chemical and/or enzymatic hydrolysis, these compounds will "cleave," thus releasing their active constituent or constituents, according to the following general scheme(s):

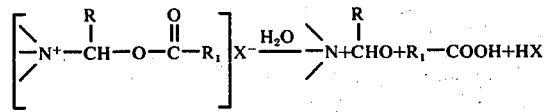

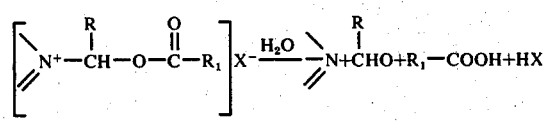

In other words, the title compounds hydrolyze (chemically or enzymatically) releasing a tertiary amine or aromatic amine derivative, an aldehyde, a carboxylic acid and a hydrogen halide (HX) per the above reaction scheme.

10 Claims, No Drawings

1-HYDROCARBONOYLOXYMETHYL-3-CARBAMOYL OR 3-CARBOETHOXY-PYRIDINIUM SALTS

BACKGROUND OF THE INVENTION

1. Field of the Invention

The present invention is directed to certain novel labile quaternary ammonium salts characterized as being transient. More particularly, the present invention extends to certain transient derivatives which could be characterized chemically as labile quaternary ammonium salts which exhibit extreme solubility and which protect its components (i.e., tertiary amine, aldehyde and carboxylic acid against oxidation, dealkylation and protonation, and yet, are predictably "cleaved" to release an active moiety and/or moieties.

For purposes of this application, the term "labile" denotes a quaternary ammonium salt of a tertiary (t) aliphatic amine or an aromatic amine which is stable in the neat state, but when placed in an aqueous or alcoholic environment (preferentially slightly basic or acidic), or in biological systems (e.g., serum, blood, liver homogenate) will undergo enzymatic and/or acid or base cleavage, thus releasing the original tertiary aliphatic amine or aromatic amine, or its proton salt.

The term "transient" pertains to a quaternary ammonium salt as described above, which, after chemical and/or enzymatic hydrolysis, will "cleave" into three moieties (tertiary aliphatic amine or an aromatic amine, or a salt thereof, an aldehyde, and a carboxylic acid) in equal molecular amounts. That is, these transient derivatives are adequate for protecting and/or solubilizing tertiary aliphatic amines or aromatic amines, aldehydes and carboxylic acids, prior to their chemical and/or enzymatic release for their intended use. Release occurs in such a manner that a sufficient amount of the compound intended to be delivered is available for its intended use.

For example, in the field of drug chemistry, and specifically, any drug containing a tertiary aliphatic amine or an aromatic amine function as described in the above generic formula, such a drug is transformed into a remarkably more soluble labile quaternary ammonium salt, which after administration is resistant to extensive metabolism at or near the tertiary or aromatic amine function, while the active tertiary or aromatic amine is released following chemical and/or enzymatic hydrolysis at its therapeutic site of action.

2. Description of the Prior Art

One of the basic methods of synthesis of the compounds encompassed within the above-described generic formula consists in reacting a compound of the formula (A) below wherein R and R₁ are defined as above with a compound of the formula (B) below, wherein R, R₁, $\equiv$N and $\geq$N and X are defined as above:

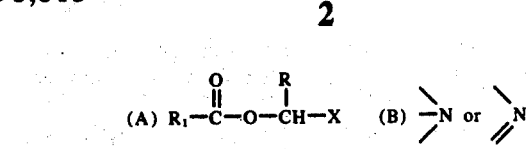

The compounds of formula (A) above are old in the art and are formed by the reaction between an aldehyde (R — CHO) and an acyl halide

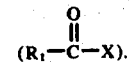

See, R. Adams and E. H. Vollweiler, *J. Amer. Chem. Soc.*, 40, 1732 (1918); H. E. French and R. Adams, ibid., 43, 651 (1921); L. H. Ulich and R. Adams, ibid., 43, 660 (1921).

Thus, preparation of the compounds of formula (A) can be described by reference to the following equation, wherein R and R₁ are defined as above:

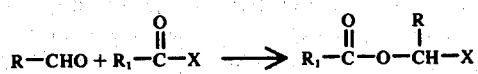

The compounds of formula (A) have been used in the past to protect a carboxy function in the following manner:

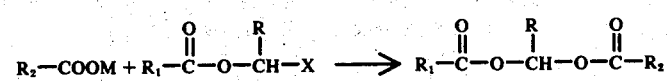

In the above equation, R and R₁ are defined as above; R₂ represents the residue of ampicillin or a salicyclic acid derivative; and M represents an alkali metal salt (Na, K, etc.). See, "Acyloxymethyl Esters of Ampicillin," W. V. Daehne, E. Fredriksen, E. Gundersen, F. Lund, P. Morch, H. J. Petersen, K. Roholt, L. Tybring, and W. V. Godfredsen, *J. Med. Chem.*, 13, 607 (1970), or British Pat. No. 1,220,457. While those compounds of formula (A) have been used as outlined above, i.e., protecting the carboxy function, this utility has no bearing on the invention disclosed and claimed herein. On the other hand, it is generally known that any activated haloalkyl compound (e.g., benzyl bromide or chloride) will react with a tertiary aliphatic amine to form the corresponding quaternary ammonium salt. However, this salt does not undergo hydrolytic cleavage, which is a necessary characteristic of the labile quaternary ammonium salts of this invention.

SUMMARY OF THE INVENTION

It is one object of the present invention to provide certain labile quaternary ammonium salts as transient derivatives, characterized by their extreme water solubility.

It is another object of the present invention to provide labile quaternary ammonium salts as described above which are protected against oxidation, dealkylation, and protonation prior to chemical and/or enzymatic hydrolysis.

Still, it is another object of the present invention to provide labile quaternary ammonium salts as described above which meet the above criteria and still are subject to chemical and/or enzymatic cleavage, thus releasing, on one hand, the original t-aliphatic amine or aromatic amine, and on the other hand, an aldehyde and a carboxylic acid.

All of the foregoing objects are attained with the following compounds generically described in formulas (I) and (II) below:

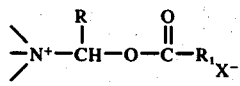

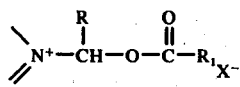

wherein $\equiv\!N$ represents a tertiary aliphatic amine; wherein $\geq\!N$ represents an aromatic amine; wherein R represents a member selected from the group consisting of a hydrogen atom, a $C_1$-$C_8$ open chain or cyclo alkyl group, a $C_1$-$C_8$ alkoxyalkyl group, a $C_1$-$C_8$ acyloxyalkyl group, a $C_1$-$C_8$ haloalkyl group, a $C_1$-$C_8$ carboxyalkyl group, an aryl group, and a substituted aryl group, whose substituents are selected from the group consisting of a halogen atom, an O-lower alkyl ($C_1$-$C_4$) group, an O-acyl group, a nitro group, a carboxyl group, and a carboethoxy group; wherein $R_1$ which may be the same or different, represents any member defined by R above with the proviso that $R_1$ cannot be a hydrogen atom; and wherein $X^-$ represents a member selected from the group consisting of a halogen atom or any other equivalent anion;

with the further proviso that $\equiv\!N$ and $\geq\!N$, respectively cannot represent trimethylamine and pyridine or quinoline when R represents a hydrogen atom and $R_1$ represents a methyl group or a phenyl group.

In the above formulas, reference to "aryl" denotes a phenyl or naphthyl group; reference to "halo" and "halogen" in each occurrence denotes any suitable member of the halogen series, e.g., chlorine, bromine or iodine; and reference to "acyl" in the expression O-acyl denotes any convenient acyl group, such as a formyl group, an acetyl group, a propionyl group, a benzoyl group, etc. It is further noted that the term "substituted" insofar as substituted aryl is concerned refers to the fact that the aryl function may be substituted with any one or more of those substituents specifically defined herein.

As stressed earlier, the compounds of this invention are extremely useful where one wishes to protect a t-amine, aromatic amine, aldehyde or carboxylic acid prior to their chemical and/or enzymatic release for their intended use.

DETAILED DESCRIPTION OF THE PREFERRED EMBODIMENTS

While all of the compounds encompassed within the above generic formula meet applicant's criteria, nevertheless, certain compounds remain preferred as set out below. Additional preferred compounds can be found in the examples which follow:

1. 1-(Benzoyloxymethyl)-3-carbamoyl-pyridinium chloride
2. 1-(α-Benzoyloxybenzyl)-3-carbamoyl-pyridinium bromide
3. 1-(Cinnamoyloxymethyl)-3-carbamoyl-pyridinium chloride
4. 1-(α-Benzoyloxyethyl)-3carbamoyl-pyridinium chloride
5. 1-(α-Cinnamoyloxyethyl)-3-carbamoyl-pyridinium chloride
6. 1-(Benzoyloxymethyl)-ethylnicotinate chloride
7. 1-(Cinnamoyloxymethyl)-ethylnicotinate chloride
8. 1-(α-Benzoyloxybenzyl)-ethylnicotinate chloride
9. 1-(α-Cinnamoyloxybenzyl)-ethylnicotinate chloride
10. Benzoyloxymethyl-triethylammonium chloride
11. α-Benzoyloxybenzyl-triethylammonium bromide
12. Cinnamoyloxymethyl-triethylammonium chloride
13. α-Benzoyloxyethyl-triethylammonium chloride
14. α-Cinnamoyloxyethyl-triethylammonium chloride
15. ω-(Diethyl-benzoyloxymethyl-ammonium)-2,6-dimethylacetanilide chloride
16. ω-(Diethyl-α-benzoyloxybenzyl-ammonium)-2,6-dimethylacetanilide chloride
17. ω-(Diethyl-cinnamoyloxymethyl-ammonium)-2,6-dimethylacetanilide chloride
18. ω-[Diethyl-(α-benzoyloxyethyl)-ammonium]-2,6-dimethylacetanilide chloride
19. ω-[Diethyl-(α-cinnamoyloxyethyl)-ammonium]-2,6-dimethylacetanilide chloride
20. N,N-dimethylglycine methyl ester-N-benzoyloxymethyl chloride
21. N,N-diethylglycine ethyl ester-N-benzoyloxymethyl chloride
22. ω-(Diethyl-pivaloyloxymethyl-ammonium)-2,6-dimethylacetanilide chloride
23. N,N-dimethylglycine methyl ester-N-pivaloyloxymethyl chloride
24. N,N-diethylglycine pyridine methanol ester-N-pivaloyloxymethyl chloride The compounds of this invention can be conveniently prepared in the manner described below:

METHOD A

React an α-halo-ester of the general formula:

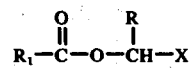

wherein R, $R_1$ and X are defined as above, directly with a tertiary aliphatic amine ($\equiv\!N$) or an aromatic amine ($\geq\!N$) in approximately equimolecular proportions, in the presence of an inert solvent (ether, acetonitrile, $CH_2Cl_2$, etc.) at room temperature or at the reflux temperature of the solvent for 2–24 hours. As an alternative procedure, the above reaction can be carried out in the absence of a solvent by mixing the above two reactants together and maintaining them at room temperature or between 20°–70° C for 2–24 hours. In both cases, the crystalline salt formed can be purified by crystallization from an ether-ethanol mixture, or the like.

METHOD B

The same compounds can be obtained by first mixing the tertiary aliphatic amine ($\equiv\!N$) or aromatic amine ($\geq\!N$) with an equimolar amount of the corresponding acyl halide

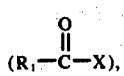

maintaining the mixture at room temperature for 2–24 hours. Then there is added to the reaction mixture an equimolecular amount of the aldehyde (R — CHO). The mixture is then stirred at room temperature or elevated temperature, up to 75° C, for 2 – 48 hours. Purification of the final product is carried out as in Method A.

In the above description of Method B, R, $R_1$ and X are defined as above.

A better understanding of the instant invention will be gained from a review of the following examples which are simply illustrative and not limitative of the invention.

EXAMPLE I

1-Benzoyloxymethyl-3-ethylcarboxyl pyridinium chloride (ethylnicotinate benzoyloxymethyl chloride)

A mixture of 3.00 g (0.02 mol) of ethyl nicotinate and 3.50 g (0.02 mol) of chloromethyl benzoate was heated under a slow stream of nirogen for 10 hours at 70° C. After 1.5 hours, the solution turned light yellow and crystals could be seen growing in toward the center of the flask. Heating of the solution was continued until it appeared that no more crystals were being formed. The mixture was cooled and titrated with ether. The solid was removed by filtration, dried and recrystallized from an ethanol-ether mixture. After drying, there were obtained 2.18 g of 1-benzoyloxymethyl-3-ethylcarboxyl pyridinium chloride.

The mp of the compound was 138°– 141° C. Analysis Calculated for $C_{16}H_{16}NO_4Cl$: C, 60.47; H, 5.08; N, 4.41. Found: C, 60.02; H, 5.05; N, 4.41. Spectra: ir (KBr) 1730 cm$^{-1}$ (s) (c=o); nmr (CDCl$_3$); δ 1.43 (t, 3, C$\underline{H}_3$CH$_2$); 4.47 (q, 2, CH$_3$C$\underline{H}_2$O); 7.7–7.3 (m, 5, —N —C$\underline{H}_2$ —O$_2$C and 3-4- and 5-H on the benzoate ring); 8.20 – 7.95 (m, 2, 2- and 6$\underline{H}$ on the benzoate ring); 9.17 – 8.50 (m, 4,- and 5 - $\underline{H}$ on the nicotinate ring), 10.0 (broad s, 1, 2 - $\underline{H}$ on the nicotinate ring) and 10.17 (broad d, 1, 3 = 5H$_z$, 6-$\underline{H}$ on the nicotinate ring).

EXAMPLE II

1-Methyl-3-(α-benzoyloxybenzyl)-imidazolium chloride (1-Methylimidazole-3-α-benzoyloxybenzyl chloride)

METHOD A

A mixture of 1.67 g (0.02 mol) of 1-methyl-imidazole and 4.93 g (0.02 mol) of α-chlorobenzylbenzoate was kept overnight in a well closed flask at 65°– 70° C. The reaction mixture was titrated with ether (approximately 150 ml) and the solid material was filtrated off. The crude material (approximately 5 g, m.p.: 165°–175° C) was recrystallized from an ethanol-ether or dichloromethane-dioxane mixture to give 4.2 g (63% yield) of 1-methyl-3-(α-benzoyloxybenzyl)-imidazolium chloride.

The mp was 199°–201° C (uncorrected). Spectra: ir (KBr) 1740 cm$^{-1}$ (s) (c=o); nmr (CDCl$_3$) δ 4.17 (s, 3, N - C$\underline{H}_3$); 8.18–7.25 (m, 12, 4- and .5 - $\underline{H}$ on imidazole and aromatic $\underline{H}$ - 5); 8.50 (s, 1, CO$_2$C$\underline{H}$ - N$^+$) and 11.1 (broad s, 1, 2 - $\underline{H}$ on imidazole).

Analysis Calculated for $C_{18}H_{17}N_2O_2Cl$: C, 65.74; H, 5.21; N, 8.52. Found: C, 65.49; H, 5.22; N, 8.68.

METHOD B

To an ether solution of benzoyl chloride (2.81 g; 0.02 mol) there was added dropwise 1.67 g (0.02 mol) of 1-methylimidazole with stirring. The resulting mixture was evaporated in vacuo and the residue was allowed to react with 2.12 g (0.02 mol) of benzaldehyde at 70° C overnight, using a CaCl$_2$ drying tube to protect it from moisture. After cooling, the reaction mixture was titrated with ether and the solid separated by filtration to give 5.28 g (m.p. 163°–178°; 80% yield) of crude 1-methyl-3-(α-benzoyloxybenzyl)-imidazolium chloride. After recrystallization from dichloromethane-dioxane, pure 1-methyl-3-(α-benzoyloxybenzyl)-imidazolim chloride was obtained. The mp of the compound was 199°–201° C. The ir and nmr spectra were identical with that of the compound obtained from Method A above.

METHOD C (variant of Method B)

The same compound, 1-methyl-3-(α-benzoyloxybenzyl)-chloride was obtained by reacting the first two components, 1-methylimidazole and benzoyl chloride, at room temperature, overnight, in absence of any solvent, then reacting the intermediar formed with benzoldehyde, as described above.

EXAMPLE III

1-Benzoyloxymethyl-1,4-diazabicyclo [2.2.2] octane chloride (1,4-diazabicyclo-[2.2.2] octane benzoyloxymethyl chloride)

A mixture of 2.24 g (0.02 mol) of 1,4-diazabycyclo [2.2.2] octane and 3.50 g (0.02 mol) of chloromethyl benzoate was allowed to react at room temperature for 48 hours. The crystalline mixture was then titrated with ether, filtered off and recrystallized from ethanol-ether. After drying, there was obtained 4.32 g (75% yield) of 1-benzoyloxymethyl-1,4-diazabicyclo [2.2.2] octane chloride.

The mp of the compound was 208°–209° C (dec.). Analysis calculated for $C_{14}H_{19}O_2NCl$: C, 59.46; H, 6.79; N, 9.91; Found: C, 59.03; H, 6.80; N, 9.73. Spectra: nmr (D$_2$O) ω 3.50 (q, 12,—N—C$\underline{H}_2$—N$^+$); 7.5–7.9 (m, 3, 3, 4- and 5 - $\underline{H}$ on the benzoate ring); 8.1–8.3 (m, 2, 2- and 6$\underline{H}$ on the benzoate ring).

EXAMPLE IV

ω-(Diethyl-benzoyloxymethyl)-ammonium-2,6-dimethylacetanilide chloride (lidocaine benzoyloxymethyl chloride)

A mixture of 4.68 g (0.02 mol) of lidocaine (ω-diethylamino-2,6-dimethylacetanilide) and 3.50 g (0.02 mol) of chloromethylbenzoate was kept under N$_2$ in a 65°–70° C oil bath for 24 hours. The crystalline mass obtained was titrated with ether, isolated by filtration and recrystallized from ethanol-ether. There was obtained 7.0 g (70% yield) of ω-diethyl-benzoyloxymethyl ammonium-2,6-dimethylacetanilide chloride.

The mp of the compound was 153°–153.5° C (dec.). Analysis calculated for $C_{22}H_{29}O_3N_2Cl$: C, 65.25; H, 7.23; N, 6.92; Found: C, 65.53; H, 7.50; N, 6.84; Spectra: nmr: ω 1.60 (t, 6, CH$_2$—C$\underline{H}_3$); 2.33 (s, 6, aryl —CH$_3$), 3.82 (q, 4, C$\underline{H}_2$-CH$_3$); 2.33 (s, 6, aryl — C$\underline{H}_3$), 3.82 (q, 4, C$\underline{H}_2$—CH$_3$);

5.22 (s, 2, N—CH$_2$—C(=O)—N);

6.08 (s, 2, —OCH$_2$—N); 7.05 (s, 3, 3, 4 and 5 H — s on lidocaine-benzene ring); 7.5–7.8 (m, 3, 3, 4- and 5 H on benzoate ring); 8.1–8.3 (m, 2, 2- and 6 H on the benzoate ring); 11.25 (5, 1, — NH).

The quaternary salts described in the following table (Examples V – XXII) are obtained by the same methods as described in Examples I to IV above. The constituent symbols R, R$_1$, ⩾N, ⩾N and X are defined as above.

TABLE I $$R-CH-N^+\diagup \quad X^-$$
$$\phantom{R-CH-}O-C-R_1$$
$$\phantom{R-CH-O-}\|$$
$$\phantom{R-CH-O-}O$$

$$R-CH-N^+\diagdown \quad X^-$$
$$\phantom{R-CH-}O-C-R_1$$
$$\phantom{R-CH-O-}\|$$
$$\phantom{R-CH-O-}O$$

| Example | R | R$_1$ | —N⩽ | X |
|---|---|---|---|---|
| V | H— | phenyl | —N(C$_2$H$_5$)$_3$ | Cl |
| VI | H— | phenyl | —N(C$_2$H$_5$)$_3$ | Br |
| VII | CH$_3$— | phenyl | —N(C$_2$H$_5$)$_3$ | Cl |
| VIII | H— | phenyl | —N-(piperidyl-3-CONH$_2$) | Cl |
| IX | phenyl | phenyl | —N-(piperidyl-3-COOC$_2$H$_5$) | Br |
| X | phenyl | phenyl—CH=CH— | —N-(piperidyl-3-COOC$_2$H$_5$) | Cl |
| XI | phenyl—CH=CH—phenyl | | —N(CH$_3$)$_3$ | Cl |
| XII | H | —C(CH$_3$)$_3$ | —N(CH$_3$)$_3$ | Cl |
| XIII | H | —C(CH$_3$)$_3$ | —N-(piperidyl-3-CONH$_2$) | Cl |

TABLE I-continued $$R-CH-N^+ \diagup \quad X^-$$
$$\underset{O}{\overset{\|}{O-C-R_1}}$$

$$R-CH-N^+ \diagup \quad X^-$$
$$\underset{O}{\overset{\|}{O-C-R_1}}$$

| Example | R | $R_1$ | $-N\diagup$ | X |
|---|---|---|---|---|
| XIV | 2-methoxyphenyl | phenyl | 3-carbamoylpiperidin-1-yl | Br |
| XV | phenyl | 4-chlorophenyl | $-N(CH_3)_2CH_2(CH_3)$ | Cl |
| XVI | H | $-C(CH_3)_3$ | 1,4-diazabicyclo[2.2.2]octan-1-yl | Cl |
| XVII | H | $-C(CH_3)_3$ | (Lidocaine) $-N(C_2H_5)_2CH_2C(O)NH$-(2,6-dimethylphenyl) | Cl |
| XVIII | phenyl | phenyl | (Pilocarpine) | Br |
| XIX | H | phenyl | Pilocarpine | Cl |
| XX | H | $-C(CH_3)_3$ | Pilocarpine | Cl |
| XXI | H | phenyl | $-N(CH_3)_2CH_2COOCH_3$ | Cl |

TABLE I-continued

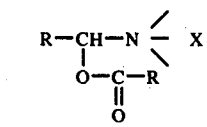

| Example | R | R | —N⟨ | X |
|---|---|---|---|---|
| XXII | H | -C(CH)(CH)CH (isopropyl-like) | -N(CH)(CH)(CH COOCH-pyridyl) | Cl |

EXAMPLE XXIII

In Vitro Cleavage of 1-Methylimidazole-3-Benzoyloxybenzyl Chloride

1-Methylimidazole-3-benzoyloxybenzyl chloride was dissolved in water. A a few drops of 1N NaOH solution was added to raise the pH to approximately 10 – 11. The smell of benzaldehyde could be detected, and after acidifying the solution, benzoic acid precpitates. The third component, 1-methylimidazole could be isolated by extraction with ether of the basified solution.

The "soft" quaternary salt thus cleaves back into the original components.

EXAMPLE XXIV

Enzymatic Release of Lidocaine From Lidocaine Benzoyloxymethyl Chloride

Lidocaine benzoyloxymethyl cloride (see Example 4) was dissolved in water. 0.5 ml of this solution (containing 50 mg of the compound) was incubated at 37 C with 5 ml of human serum. Analysis of the solution after 30 minutes (be LC) indicated a complete cleavage of the quaternary salt, by 100% recovery of the lidocaine.

The preceding examples (I – XXII) can be repeated with similar success by simply substituting the generically or specifically described reactants and/or operating conditions of this invention for those used in the preceding examples.

Similar results as obtained for the labile quaternary salts of Examples XXIII and XXIV will be obtained for the remaining compounds of the instant invention when tested under in vitro or in vivo conditions.

From the foregoing description, one of ordinary skill in the art can easily ascertain the essential characteristics of the instant invention, and without departing from the spirit and scope thereof, can make various changes and modifications of the invention to adapt it to various usages and conditions. As such, these changes and modifications are properly, equitably, and intended to be, within the full range of equivalence of the following claims.

What I claim is:

1. A soft quaternary compound of the formula (I):

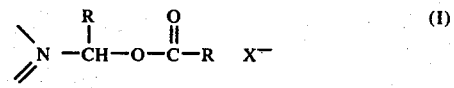

wherein ⟩N represents 3-carbamoyl-pyridyl or ethylnicotinyl; wherein R represents a member selected from the group consisting of hydrogen, C -C open chain or cyclo alkyl, C -C alkoxyalkyl, C -C acyloxyalkyl, C -C haloalkyl, C -C carboxyalkyl, phenyl, naphthyl, and substituted phenyl or naphthyl, the substituents of which are selected from the group consisting of halogen, O-loweralkyl (C -C ), O-formyl, O-acetyl, O-propionyl, O-benzoyl, nitro, carboxyl, and carboethoxy; wherein R which may be the same or different, represents any member defined by R above with the proviso that R cannot be hydrogen; and wherein X⁻ represents a member selected from the group consisting of halogen or any other equivalent anion and a soft quaternary compound selected from the group consisting of II) 1-(cinnamoyloxymethyl)-3-carbamoyl-pyridinium chloride, III) 1-(alpha-cinnamoyloxyethyl)-3-carbamoyl-pyridinium chloride, IV) 1-(cinnamoyloxymethyl)-ethylnicotinate chloride and V) 1-(alpha-cinnamoyloxybenzyl)-ethylnicotinate chloride.

2. The compound of claim 1:
   1-(Benzoyloxymethyl)-3-carbamoyl-pyridinium chloride.

3. The compound of claim 1:
   1-( -Benzoyloxybenzyl)-3-carbamoyl-pyridinium bromide.

4. The compound of claim 1:
   1-(Cinnamoyloxymethyl)-3-carbamoyl-pyridinium chloride.

5. The compound of claim 1:
   1-( -Benzoyloxyethyl)-3-carbamoyl-pyridinium chloride.

6. The compound of claim 1:
   1-( -Cinnamoyloxyethyl)-3-carbamoyl-pyridinium chloride.

7. The compound of claim 1:
1-(Benzoyloxymethyl)-ethylnicotinate chloride.
8. The compound of claim 1:
1-(α-Benzoyloxybenzyl)-ethylnicotinate chloride.
9. The compound of claim 1:
1-(Cinnamoyloxymethyl)ethylnicotinate chloride.
10. The compound of claim 1:
1-(α-Cinnamoyloxybenzyl)-ethylnicotinate chloride.

* * * * *

UNITED STATES PATENT OFFICE
CERTIFICATE OF CORRECTION

Patent No. 3,998,815                Dated December 21, 1976

Inventor(s) NICOLAE S. BODOR

It is certified that error appears in the above-identified patent and that said Letters Patent are hereby corrected as shown below:

IN THE CLAIMS:

Claim 1, lines 35, 36 and 37, reference to "C-C" should read --$C_1$-$C_8$--; line 40, reference to "(C-C)" should read --($C_1$-$C_4$)--.

Signed and Sealed this

Fourteenth Day of June 1977

[SEAL]

Attest:

RUTH C. MASON
Attesting Officer

C. MARSHALL DANN
Commissioner of Patents and Trademarks